US012799154B2

(12) United States Patent
Messina et al.

(10) Patent No.: US 12,799,154 B2
(45) **Date of Patent: *Nov. 17, 2026**

(54) PROCESS FOR PREPARING HIGH PURITY ALLOPREGNANOLONE AND INTERMEDIATES THEREOF

(71) Applicant: CURIA SPAIN, S.A.U., Boecillo (ES)

(72) Inventors: Ivano Messina, Boecillo (ES); Jesús Miguel Iglesias Retuerto, Boecillo (ES); Ana María Ares Sacristán, Boecillo (ES)

(73) Assignee: CRYSTAL PHARMA S.A.U., Boecillo (ES)

( * ) Notice: Subject to any disclaimer, the term of this patent is extended or adjusted under 35 U.S.C. 154(b) by 1097 days.

This patent is subject to a terminal disclaimer.

(21) Appl. No.: 17/440,378

(22) PCT Filed: Mar. 18, 2020

(86) PCT No.: PCT/EP2020/057387

§ 371 (c)(1),
(2) Date: Sep. 17, 2021

(87) PCT Pub. No.: WO2020/187965

PCT Pub. Date: Sep. 24, 2020

(65) Prior Publication Data

US 2022/0162255 A1 May 26, 2022

(30) Foreign Application Priority Data

Mar. 19, 2019 (EP) .................................... 19382193

(51) Int. Cl.
*C07J 9/00* (2006.01)
*C07J 7/00* (2006.01)

(52) U.S. Cl.
CPC ................. *C07J 9/00* (2013.01); *C07J 7/009* (2013.01)

(58) Field of Classification Search
CPC .................................. C07J 9/00; C07J 7/009
See application file for complete search history.

(56) References Cited

U.S. PATENT DOCUMENTS

| | | | | |
|---|---|---|---|---|
| 4,061,661 | A | 12/1977 | Wiechert et al. | |
| 5,232,917 | A * | 8/1993 | Bolger | C07J 21/00 540/110 |
| 12,209,107 | B2 | 1/2025 | Messina et al. | |
| 2014/0058079 | A1 | 2/2014 | Mensah-Nyagan et al. | |
| 2020/0087341 | A1 | 3/2020 | Torregrossa | |

FOREIGN PATENT DOCUMENTS

| | | | |
|---|---|---|---|
| CN | 103396467 | A | 11/2013 |
| WO | 93/03732 | A1 | 3/1993 |
| WO | 2009/108804 | A2 | 9/2009 |
| WO | 2012/127176 | A1 | 9/2012 |
| WO | 2016/164763 | A1 | 10/2016 |

OTHER PUBLICATIONS

Machine translation (Google Translate) of J.V. Euw et al., 3α, 17α, 21-Trihydroxy-5α-pregan-20-on und Subst. TR 1018, Helv. Chim . Acta, 1962, vol. 45(1). 229-230, translated on Feb. 4, 2025.*
Registry No. 148256-40-0, File REGISTRY on STN, entered STN Jun. 23, 1993.*
Herschfield et al., Journal of the American Chemical Society, 95:12, Jun. 13, 1973, pp. 3994-4002.*
Asahara et al., Solvent Handbook, Kodansha Ltd., pp. 47-51, (1985).
Ashizawa, Optimization of salt and crystal forms and crystallization techniques, Pharm Tech Japan, vol. 18, No. 10, pp. 81-96 (2002).
Dodge et al., Effect of the Acidic Component on the Mitsunobu Inversion of a Sterically Hindered Alcohol, The Journal of Organic Chemistry, vol. 59, No. 1, pp. 234-236 (1994).
Martin et al, Efficacious Modification of the Mitsunobu Reaction for Inversions of Sterically Hindered Secondary Alcohols, Tetrahedron Letters, vol. 32, No. 26, 3017-3020 (1991).
Saïah et al., The Use of Chloroacetic Acid in the Mitsunobu Reaction, Tetrahedron Letters, vol. 33, No. 30,4317-4320 (1992).
Tsunoda et al., Development of New Mitsunobu Reagents, Journal of Synthetic Organic Chemistry, Japan, vol. 55, No. 7, pp. 631-641 (1997).
Vojtech Kapras et al., Preparation of Steroid Sulfamates and Their Interaction with GABA(A) Receptor, Coll. Czech. Chem. Comm., 2009, vol. 74(4), 643-650.
David K Fukushima et al., Studies in Steroid Metabolism, XXV. Isolation and Characterization of New Urinary Steroids, J. Biol. Chem., 1954, vol. 210(1), 129-137.
J. V. Euw et al., 3α, 17α, 21-Trihydroxy-5α-pregnan-20-on und Subst. TR 1018, Helv. Chim. Acta, 1962, vol. 45(1), 224-232.
H. Hirschmann et al., Chemical Interrelationships Between Some 20-Hydroxysteroids, J. Biol. Chem., 1951, vol. 192(1), 115-129.
R. B. Moffett et al., 17-Isopregnan-3(α)-ol-20-one, JACS, 1944, vol. 66(12), 2098-2100.
A. H. Soloway et al., Differential Reduction of Steroid Ketones, JACS, 1953, vol. 75(10), 2356-2358.
R. H. Purdy et al., Synthesis, Metabolism, and Pharmacological Activity of 3a-Hydroxy Steroids Which Potentiate GABA-Receptor-Mediated Chloride Ion Uptake in Rat Cerebral Cortical Synaptoneurosomes, J. Med. Chem., 1990, vol. 33 6), 1572-1581.
Mancera et al., Steroids, XLIII. A Ten Step Conversion of Progesterone to Cortisone. The Differential Reduction of Pregnane-3,20-diones with Sodium Borohydride, Journal of the American Chemical Society, Mar. 20, 1953, vol. 75, pp. 1286-1290.
Tsunoda et al., Mitsunobu Acylation of Sterically Congested Secondary Alcohols by *N,N,N',N'*-Tetramethylazodicarboxamide-Tributylphosphine Reagents, Tetrahedron Letters, 1995, vol. 36, No. 14, pp. 2529-2530.

(Continued)

*Primary Examiner* — Rebecca L Anderson
(74) *Attorney, Agent, or Firm* — Casimir Jones, S.C.; Tristan A. Fuierer

(57) ABSTRACT

The invention relates to an efficient and industrially applicable process for the preparation and purification of allopregnanolone and intermediates thereof without the assistance of column chromatography.

13 Claims, No Drawings

(56) References Cited

OTHER PUBLICATIONS

Acidity of Alcohols, Libretexts <https://chem.libretexts.org/Bookshelves/Organic_Chemistry/ Supplemental_Modules_(Organic_Chemistry)/Alcohols/Properties_of_Alcohols/Acidities_of Alcohols#:-:text=A>, pp. 1-2, downloaded Jan. 18, 2023.

Varasi et al., J. Org. Chem. 52(19), pp. 4235-4238 (1987).

* cited by examiner

PROCESS FOR PREPARING HIGH PURITY ALLOPREGNANOLONE AND INTERMEDIATES THEREOF

CROSS-REFERENCE TO RELATED APPLICATIONS

This application is filed under the provisions of 35 U.S.C. § 371 and claims the priority of International Patent Application No. PCT/EP2020/057387 filed on 18 Mar. 2020 entitled "PROCESS FOR PREPARING HIGH PURITY ALLOPREGNANOLONE AND INTERMEDIATES THEREOF" in the name of Ivano MESSINA, et al., which claims priority to European Patent Application No. 19382193.1, filed on 19 Mar. 2019.

FIELD OF THE INVENTION

The invention belongs to the field of drug synthesis, and more particularly relates to an efficient and industrially applicable process for the preparation and purification of allopregnanolone and to intermediates useful therefor.

BACKGROUND OF THE INVENTION

Allopregnanolone [516-54-1], also known as 3α-hydroxy-5α-pregnan-20-one, 5α-pregnan-3α-ol-20-one or 3α,5α-tetrahydroprogesterone (3α,5α-THP), as well as brexanolone (USAN), is an endogenous inhibitory pregnane neurosteroid. Synthesized from progesterone in the brain, it is a potent positive allosteric modulator of the action of γ-aminobutyric acid (GABA) at GABA-A receptor. Allopregnanolone has effects similar to those of other positive allosteric modulators of the GABA action at GABA-A receptor such as the benzodiazepines, including anxiolytic, sedative, and anticonvulsant activity. The structure of allopregnanolone is depicted below.

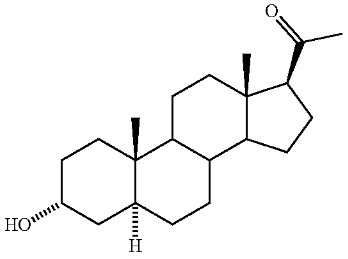

Allopregnanolone

Brexanolone injection for intravenous use (brexanolone IV) is a novel product developed by Sage Therapeutics for the treatment of postpartum depression (PPD), a serious and potentially life-threatening condition, for which no current pharmacotherapies are specifically indicated. FDA approval for brexanolone IV is expected for March 2019.

Several methods have been disclosed in the state of the art for the synthesis of this compound.

Purdy et al. (J. Med. Chem. 1990, 33, 1572-1581) described the direct preparation from isoallopregnanolone, an epimer to allopregnanolone, structurally differing only in the orientation of the hydroxyl group at carbon 3 of the steroid A-ring. The inversion of the 3β-hydroxy group was achieved by means of a Mitsunobu reaction employing trifluoroacetic acid (TFA), in the presence of triphenylphosphine ($PPh_3$) and diethyl azodicarboxylate (DEAD), without isolation of the intermediate trifluoroacetate ester (Scheme 1). The crude product was worked-up and crystallized to remove a 5% of unreacted starting material (1), yielding allopregnanolone (2a) in 74% yield, mp 168-170° C. The product was further purified by dry column chromatography on silica gel and crystallized from aqueous ethanol; yield 54%, mp 174-176° C.

Scheme 1

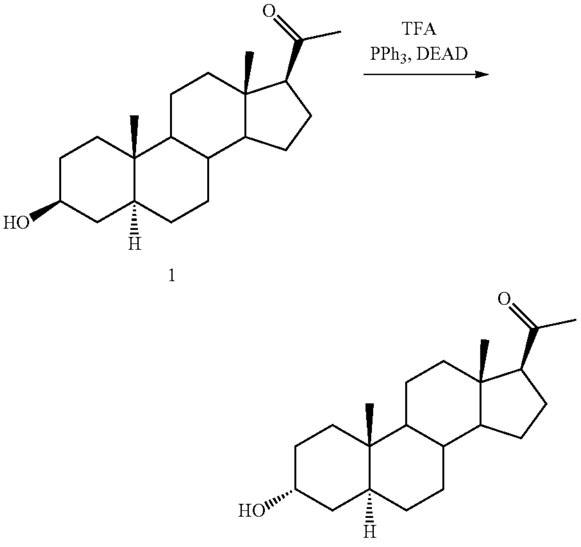

1

2a

WO 2009/108804 discloses in example 6 a similar procedure for the preparation of allopregnanolone (14) from isoallopregnanolone (12) without isolation of the intermediate trifluoroacetate ester (Scheme 2). After purification by silica column, allopregnanolone was obtained in 92% overall yield.

Scheme 2

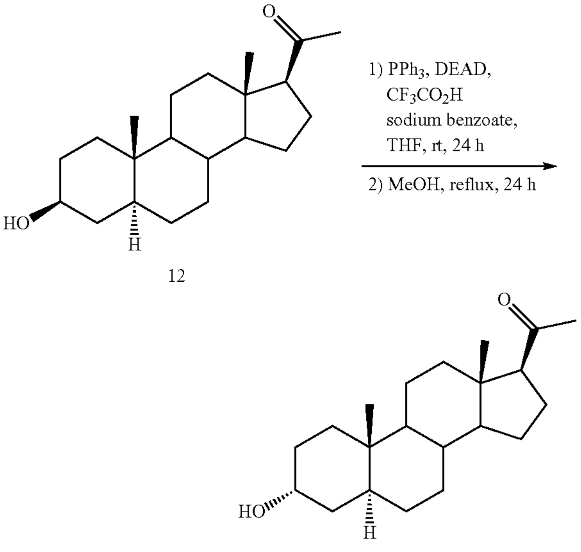

12

14

Processes including the isolation of the intermediate Mitsunobu ester have been also proposed such as for instance in WO 93/03732, WO 2012/127176 and CN 103396467 (Schemes 3, 4 and 5, respectively).

In example 4 of WO 93/03732 isoallopregnanolone was reacted with acetic acid, triphenylphosphine ($PPh_3$) and diisopropyl azodicarboxylate (DIAD) and the product residue was purified by flash chromatography on silica gel to give 3α-acetoxy-5α-pregnan-20-one in 97.5% yield. The ester was hydrolyzed with perchloric acid, leaving the reaction mixture stirring for three days to give crude allopregnanolone as disclosed in example 5.

Scheme 3

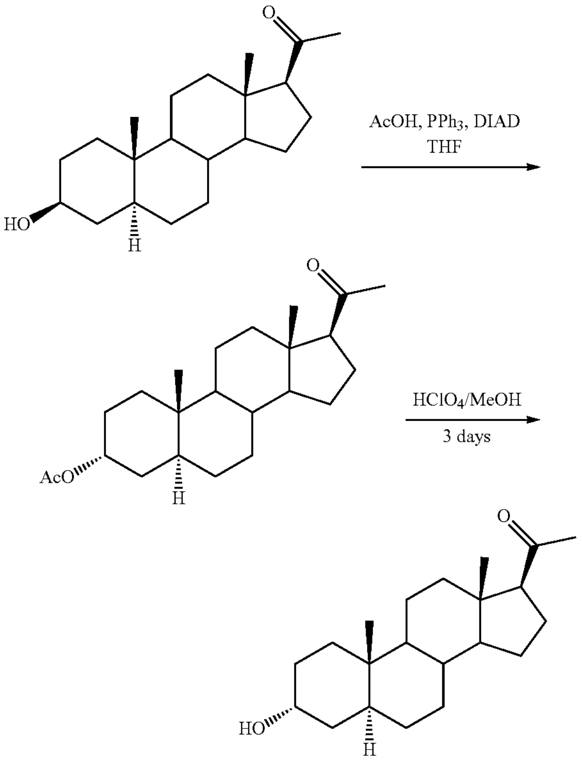

WO 2012/127176 discloses in example 4 the reaction of isoallopregnanolone with benzoic acid, triphenylphosphine ($PPh_3$) and diisopropyl azodicarboxylate (DIAD) to give a crude residue which was subjected to purification by chromatography, yielding the corresponding benzoate (3) in 90% yield. The hydrolysis was carried out in example 5 under severe conditions (KOH, MeOH for 2.5 h at reflux) followed by purification by chromatography, yielding allopregnanolone (4) in 80% yield (mp 161.7-162.8° C.). The low melting point reflects that the product could not be purified enough.

Scheme 4

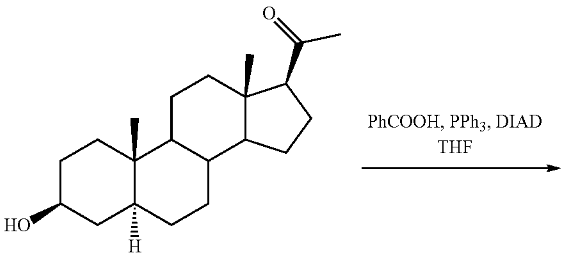

-continued

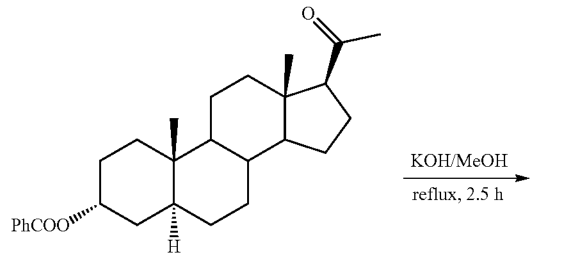

3

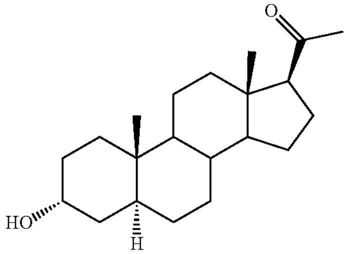

4

CN 103396467 discloses in example 5 the conversion of isoallopregnanolone into allopregnanolone by using o-methoxybenzoic acid along with triphenylphosphine ($PPh_3$) and diisopropyl azodicarboxylate (DIAD). In this procedure, the crude intermediate ester was precipitated and subjected to hydrolysis with sodium hydroxide in methanol for 2 h at 60° C. to obtain a white solid in 52% overall yield for the two steps.

Scheme 5

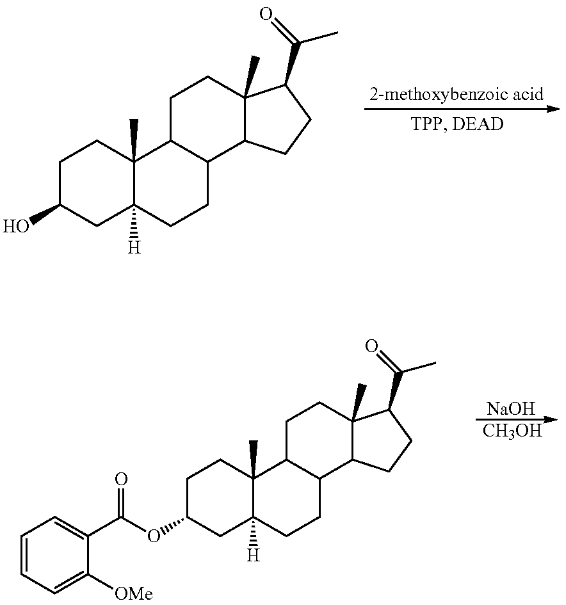

-continued

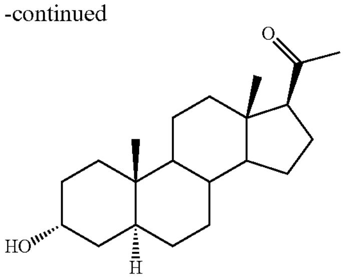

Like any synthetic compound, allopregnanolone can contain extraneous compounds or impurities. These impurities may include unreacted starting materials, byproducts of the reaction, products of side reactions, and/or degradation products. Impurities in allopregnanolone or any active pharmaceutical ingredient ("API") are undesirable and, in extreme cases, might even be harmful to a patient being treated with a dosage form of the API. Therefore, identifying impurities of an API produced in a manufacturing process and reducing/eliminating the presence of the same in the final product is crucial for commercialization.

The present inventors have thoroughly examined the processes disclosed in the cited documents and have found that they did not reproducibly yield allopregnanolone in a sufficiently pure state and/or require chromatographic purification steps. Purification by column chromatography is unsuitable, or at least undesirable, for the industrial scale manufacture of a large amount of API, an extremely large amount of solvent is required which makes the process expensive and is disadvantageous because of environmental protection.

A need thus exists to develop processes suitable for the production of highly pure allopregnanolone at commercial scale.

SUMMARY OF THE INVENTION

The present invention solves the aforementioned need by the provision of a simple and industrially applicable process for the preparation and purification of allopregnanolone and intermediates thereof. The process provided in the present invention allows obtaining highly pure allopregnanolone and intermediates thereof without the assistance of column chromatography. The present invention also provides novel intermediates useful for the preparation of allopregnanolone.

After extensive research, the present inventors have identified two important impurities associated with the methods reported in the state of the art for preparing allopregnanolone from isoallopregnanolone through the Mitsunobu reaction and subsequent hydrolysis. These undesirable impurities are 5α-pregn-2-en-20-one (herein also referred to as impurity I or elimination impurity) and 3α-hydroxy-5α,17α-pregnan-20-one (herein also referred to as impurity II or epimeric impurity).

The present inventors have conducted extensive experimentation with an intention to reduce/eliminate such impurities and obtain allopregnanolone in high purity form. As a result of this research, the inventors have surprisingly found a new methodology based on the following key features: careful selection of the acid to be reacted with isoallopregnanolone, isolation and purification of the intermediate ester by means of a specific non-chromatographic procedure, and careful selection of the final hydrolysis conditions.

Thus, in a first aspect, the invention is directed to a process for preparing and purifying a 3-carboxylic ester of allopregnanolone which comprises:

- reacting isoallopregnanolone with a strong carboxylic acid (e.g. a carboxylic acid having a pka≤3) under Mitsunobu conditions;
- precipitating the 3-carboxylic ester of allopregnanolone in a solvent system comprising water and an organic solvent; and
- recrystallizing the precipitate of the 3-carboxylic ester of allopregnanolone in a non-polar solvent.

In another aspect, the invention is directed to a process for preparing allopregnanolone which comprises:

- obtaining a 3-carboxylic ester of allopregnanolone by the above-defined process; and
- subjecting the 3-carboxylic ester of allopregnanolone thus obtained to hydrolysis under neutral conditions (e.g. with an alcohol without the assistance of any acid or base), mild basic conditions (e.g. with a base whose conjugate acid has a pKa equal or below 11) or energetic basic conditions (e.g. with a base whose conjugate acid has a pKa equal or above 12 for a time and at a temperature suitable to keep the level of 3α-hydroxy-5α,17α-pregnan-20-one in an amount of 0.5% or less).

Optionally, the process further comprises a step of purification of the allopregnanolone, e.g. by recrystallization.

In another aspect, the invention is directed to allopregnanolone or a 3-carboxylic ester of allopregnanolone, said compound being obtainable according to one process as disclosed herein.

In another aspect, the invention is directed to a 3-carboxylic ester of allopregnanolone of high purity level, and more particularly, containing an amount of 5α-pregn-2-en-20-one of 0.5% or less.

In another aspect, the invention is directed to allopregnanolone of high purity level, and more particularly, containing an amount of 5α-pregn-2-en-20-one and 3α-hydroxy-5α,17α-pregnan-20-one, in total, of 0.15% or less.

In another aspect, the invention is directed to a 3-carboxylic ester of allopregnanolone selected from:

- 2,6-dinitrobenzoate ester,
- 2,4-dinitrobenzoate ester,
- Chloroacetate ester,
- Dichloroacetate ester,
- Trichloroacetate ester,
- Cyanoacetate ester,
- Fluoroacetate ester,
- Difluoroacetate ester, and
- O-nitrobenzoate ester.

These aspects and preferred embodiments thereof are additionally also defined hereinafter in the detailed description and in the claims.

DETAILED DESCRIPTION OF THE INVENTION

The present inventors have developed a chromatography-free process for the preparation of highly pure allopregnanolone. The process of the present invention is simple, inexpensive, reproducible and is well suited for industrial scale.

Definitions

As used herein, the term "about" means a slight variation of the value specified, preferably within 10 percent of the value specified. Nevertheless, the term "about" can mean a higher tolerance of variation depending on for instance the experimental technique used. Said variations of a specified value are understood by the skilled person and are within the context of the present invention. Further, to provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value.

By “room temperature” or its abbreviation “rt” is meant herein that the reactions or processes are performed without heating or cooling. Generally, by room temperature may be understood as a temperature between about 15° C. and about 30° C., or more particularly between about 20° C. and about 25° C.

The term “organic solvent” includes for example cyclic and acyclic ethers (e.g. $Et_2O$, $iPr_2O$, $tBu_2O$, MeOtBu, 1,4-dioxane, tetrahydrofuran, methyltetrahydrofuran), hydrocarbon solvents (e.g. pentane, hexane, cyclohexane, heptane), halogenated solvents (e.g. dichloromethane, chloroform), aromatic solvents (e.g. toluene, xylene), ketones (e.g. acetone, butanone, pentanone, methyl ethyl ketone, ethyl isopropyl ketone), esters (e.g. EtOAc, iPrOAc), nitriles (e.g. acetonitrile, benzonitrile, propionitrile), amides (e.g. DMF, DMA, HMPA), alcohols (e.g. methanol, ethanol, propanol, isopropanol, sec-butanol, t-butanol), sulfoxides (DMSO) and mixtures thereof.

The term “water soluble solvent” refers to solvents capable mixing with water fully i.e. in all proportions, or partly i.e. in some proportions. Water soluble solvents include for instance organic solvents of which 5 g or more is soluble in 100 g of water at a temperature of 25° C. In a particular embodiment, the water soluble solvent is selected from an organic solvent having a miscibility in water greater than 50% by weight at 25° C.

As used herein, the term “non-polar solvent” refers to a solvent of sufficiently low polarity to induce crystal formation of a polar compound such as a 3-ester of allopregnanolone. Having regard to the present disclosure, the selection of suitable non-polar solvents is well within the knowledge of the skilled artisan. More particularly, the term “non-polar solvent” refers to a solvent having Log P>2. Non polar solvents have low dielectric constants, such as <5. In an embodiment, the non-polar solvent is selected from the group consisting of hydrocarbon solvents (e.g. pentane, hexane, cyclohexane, heptane), aromatic solvents (e.g. toluene, xylene) and cyclic and acyclic ethers (e.g. $Et_2O$, $iPr_2O$, $tBu_2O$, MeOtBu, 1,4-dioxane, tetrahydrofuran, methyltetrahydrofuran).

The term “Mitsunobu conditions” refers to conditions suitable for performing the conversion of isoallopregnanolone into a 3-carboxylic ester of allopregnanolone by reaction with particular carboxylic acids. The reagents used for Mitsunobu conditions are preferably a phosphine (typically triphenyl phosphine ($PPh_3$)), an azodicarboxylate, and an optional tertiary amine additive. Examples of azodicarboxylate include, but are not limited to, diethyl azodicarboxylate (DEAD), diisopropyl azodicarboxylate (DIAD), di-t-butyl azodicarboxylate, 1,1'-(azocarbonyl)dipiperidine, dibenzyl azodicarboxylate, and/or the like. In some embodiments, the reagents for Mitsunobu conditions may be selected such that the reagents may be recycled or recovered after the reaction is complete. In some embodiments, one or more of dicyclohexylphenylphosphine, diethylphenylphosphine, tributylphosphine, diphenyl-2-pyridylphosphine, 4-(dimethylamino)phenyldiphenylphosphine, isopropyldiphenylphosphine, tri-tert-butylphosphine, tri-n-octylphosphine, tricyclohexylphosphine, polystyryldiphenylphosphine and/or the like may be used instead of triphenyl phosphine. In some embodiments, the triphenyl phosphine, or an equivalent thereof and/or the azodicarboxylate may be anchored to a resin such as, for example, as polystyrene resin. In some embodiments, cyanomethylenetri-n-butylphosphorane may be used as a reagent for Mitsunobu conditions.

The term “neutral conditions” preferably refers to use in the hydrolysis reaction of an alcohol such as MeOH, EtOH without adding any acid or base (transesterification).

The term “mild basic conditions” preferably refers to the use in the hydrolysis reaction of a base whose conjugate acid has a pKa equal or below 11. Suitable bases include, but are not limited to, alkali and alkaline earth carbonates and bicarbonates such as potassium carbonate, sodium carbonate, barium carbonate, cesium carbonate, potassium hydrogenocarbonate, and sodium hydrogenocarbonate.

The term “energetic basic conditions” preferably refers to the use in the hydrolysis reaction of a base whose conjugate acid has a pKa equal or above 12 for short times and/or at low temperatures so as to avoid that 3α-hydroxy-5α,17α-pregnan-20-one is generated in an amount higher than 0.5%. Having regard to the present disclosure, the selection of suitable times and temperatures is well within the knowledge of the skilled artisan. Suitable bases include, but are not limited to, alkali and alkaline earth $C_{1-6}$ alkoxides and hydroxides such as potassium methoxide, sodium methoxide, potassium ethoxide, sodium ethoxide, lithium hydroxide, potassium hydroxide, sodium hydroxide, and calcium hydroxide.

Unless otherwise stated, references to purity may be understood as HPLC purity.

Preparation and Purification of 3-Esters of Allopregnanolone from Isoallopregnanolone In reproducing the conditions disclosed in the prior art, the present inventors noted that the adequate selection of the carboxylic acid to be reacted with isoallopregnanolone is important to avoid/reduce the formation of impurities, especially during the hydrolysis subsequent to the Mitsunobu reaction. Keeping the level of impurities within acceptable limits makes possible to purify both the intermediate 3-carboxylic ester and allopregnanolone without relying on column chromatography. It has been also found that isolation and purification of the intermediate ester is required in order to get a process suitable for large scale production of highly pure allopregnanolone. If the intermediate ester is not purified from certain impurities, but used in crude form for the subsequent hydrolysis reaction, then an effective purification of the final allopregnanolone turns out to be infeasible.

Specifically, the inventors have found that the Mitsunobu reaction always brings about a substantial amount, normally about 7-17%, of 5α-pregn-2-en-20-one (herein also referred to as impurity I or elimination impurity):

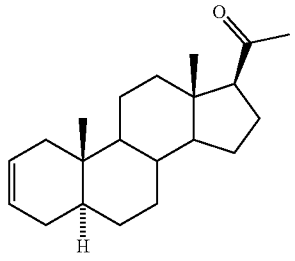

Elimination impurity I $^1H$ NMR (400 MHz, $CDCl_3$): δ 5.57 (2H), 2.50 (1H), 2.10-2.18 (1H), 2.09 (3H), 1.81-2.0 (3H), 1.51-1.71 (5H), 1.07-1.43 (9H), 0.83-0.94 (1H), 0.75-0.76 (1H), 0.73 (3H), 0.59 (3H).

$^{13}C$ NMR (400 MHz, $CDCl_3$): δ 209.7, 125.9, 125.8, 63.9, 56.8, 54.0, 44.2, 41.5, 39.9, 39.2, 35.7, 34.7, 31.8, 31.6, 30.3, 28.7, 24.5, 22.9, 21.0, 13.5, 11.8.

The elimination impurity is thus intrinsic to the Mitsunobu reaction. Attempts to prepare allopregnanolone without isolating and purifying the intermediate 3-ester failed or afforded unsatisfactory results due to the need of subjecting the final product to a complex column chromatography that does not lead to an acceptable degree of purity.

The present invention provides a method for the preparation and purification of 3-esters of allopregnanolone from isoallopregnanolone, said method comprising in a preferred embodiment:

treating isoallopregnanolone with an organic acid having a pka of 3 or less under Mitsunobu conditions;

precipitating the crude reaction mixture in a solvent system comprising a mixture of water and an organic solvent; and recrystallizing the precipitate in a non-polar solvent.

The election of an organic acid having a low pka is crucial, especially because it makes possible to subsequently conduct a clean hydrolysis of the 3-ester of allopregnanolone. For instance, it has been found that formic acid (pka=3.75), benzoic acid (pKa=4.20), acetic acid (pKa 4.75), orthometoxybenzoic acid (pKa=4.09), 3-nitrobenzoic acid (pKa 3.46), 4-nitrobenzoic acid (pKa 3.43) are unsuitable. In an embodiment, the carboxylic acid having a pka 3 is selected from the group consisting of mono-, di-, and trifluoroacetic acid, mono-, di-, and trichloroacetic acid, cyanoacetic acid, 2-nitrobenzoic acid and dinitrobenzoic acid (e.g. 2,4-, 2,6- and 3,5-dinitrobenzoic acid). In a more particular embodiment, the carboxylic acid is chloroacetic acid or dinitrobenzoic acid. Typically, the amount of carboxylic acid is about 1-4 eq, more particularly about 2-3 eq.

Suitable Mitsunobu conditions preferably comprise a phosphine such as $PPh_3$, an azodicarboxylate, and an optional tertiary amine additive. The phosphine may be selected for instance from the group consisting of triphenylphosphine, dicyclohexylphenylphosphine, diethylphenylphosphine, tributylphosphine, diphenyl-2-pyridylphosphine, 4-(dimethylamino)phenyldiphenylphosphine, isopropyldiphenylphosphine, tri-tert-butylphosphine, tri-n-octylphosphine, tricyclohexylphosphine, polystyryldiphenylphosphine or a mixture thereof. The azodicarboxylate may be selected for instance from the group consisting of diethyl azodicarboxylate (DEAD), diisopropyl azodicarboxylate (DIAD), di-t-butyl azodicarboxylate, 1,1'-(azocarbonyl)dipiperidine, dibenzyl azodicarboxylate or a mixture thereof. According to a preferred embodiment, the reagents used for the Mitsunobu reaction are or comprise triphenyl phosphine ($PPh_3$) and azodicarboxylate selected from DEAD and DIAD. Suitable amounts of phosphine and azodicarboxylate normally range about 1-2 eq. In a particular embodiment, about 1.5 eq phosphine and about 1.4 eq azodicarboxylate are added. Preferably, the azodicarboxylate, normally a solution of azodicarboxylate, is added slowly or dropwise to the reaction mixture comprising isoallopregnanolone, phosphine and organic acid. In a particular embodiment, the Mitsunobu reaction is carried out in the presence of NaOBz (e.g. about 1-2 eq).

The Mitsunobu reaction is normally carried out in the presence of an organic solvent which may be selected for instance from the group consisting of cyclic and acyclic ethers (e.g. $Et_2O$, $iPr_2O$, $tBu_2O$, MeOtBu, 1,4-dioxane, tetrahydrofuran, methyltetrahydrofuran), halogenated solvents (e.g. dichloromethane, chloroform), and aromatic solvents (e.g. toluene, xylene) or a mixture thereof. In a preferred embodiment, the solvent is selected from tetrahydrofuran (THF), 1,4-dioxane, toluene and dichloromethane or a mixture thereof; even more preferably, the solvent is tetrahydrofuran (THF), 1,4-dioxane, or toluene. In particular embodiments, the solvent is 1,4-dioxane or a mixture of 1,4-dioxane and tetrahydrofuran (THF).

In an embodiment, isoallopregnanolone is treated with the organic acid at a suitable temperature of about 0-45° C. (e.g. about 15-45° C.) for time sufficient for ester formation, normally between about 1-24 h and more particularly between about 2-12 h or about 4-8 h. In an embodiment, the reaction mixture may be stirred for sufficient time and at suitable temperature for the completion of ester formation. The reaction may be followed by thin layer chromatography (TLC or HPLC or UPLC).

After completion, water is preferably added to the crude reaction mixture and the resulting suspension may be filtered to obtain a wet cake containing a 3-carboxylic ester of allopregnanolone.

With solvents not miscible with water, it is necessary to remove the solvent, preferably by evaporation, and replace it with a solvent miscible with water (water-soluble solvent), such as 1,4-dioxane, MeOH, EtOH, IPA, ACN, etc. before adding the water.

Isolation of the 3-ester of allopregnanolone is carried out according to the present invention by precipitation in a solvent system comprising water and an organic solvent. Such a precipitation allows reducing/eliminating polar and basic impurities such as byproducts derived from the phosphine and the azodicarboxylate.

Preferably, the organic solvent used for precipitating the crude 3-ester is a water-soluble solvent such as cyclic and acyclic ethers (e.g. 1,4-dioxane), ketones (e.g. acetone, methyl ethyl ketone), nitriles (e.g. acetonitrile, propionitrile), amides (e.g. DMF, DMA, HMPA), alcohols (e.g. methanol, ethanol, propanol, isopropanol), and mixtures thereof. More particularly, the water-soluble solvent is selected from 1,4-dioxane, acetone, acetonitrile, DMF, methanol, ethanol, isopropanol or their mixtures, even more particularly the water-soluble solvent is 1,4-dioxane, acetonitrile or isopropanol, and even still more particularly, it is 1,4-dioxane.

Different proportions of water and organic solvent may be used. According to one embodiment, the ratio water to organic solvent within the solvent system ranges from about 0.1:1 to 1:0.1, more particularly about 0.2:1 to 1:0.2, 0.3:1 to 1:0.3, 0.4:1 to 1:0.4, 0.5:1 to 1:0.5, 0.6:1 to 1:0.6, 0.7:1 to 1:0.7, 0.8:1 to 1:0.8, 0.9:1 to 1:0.9, and about 1:1.

In more specific embodiment, the crude 3-ester of allopregnanolone may be conveniently precipitated with a solvent system comprising water and an organic solvent at a ratio about 1:1, wherein the organic solvent is 1,4-dioxane, acetonitrile or isopropanol.

Once precipitated, the 3-ester of allopregnanolone is preferably dried (e.g. under reduced pressure).

Purification of the 3-ester of allopregnanolone is effected using recrystallization in a non-polar solvent. Advantageously, the recrystallization allows eliminating or reducing the amount of 5α-pregn-2-en-20-one (i.e. impurity I or elimination impurity) to about 0.5% or below (e.g. about 0.4% or below, 0.3% or below, 0.2% or below, 0.1% or below). Examples of non-polar solvents useful for inducing crystal formation include, but are not limited to, hydrocarbon solvents (e.g. pentane, hexane, cyclohexane, heptane), aromatic solvents (e.g. toluene, xylene) and cyclic and acyclic ethers (e.g. $Et_2O$, $iPr_2O$, $tBu_2O$, MeOtBu, methyltetrahydrofuran). In a particular embodiment, the non-polar solvent is selected from the group consisting of hexane, cyclohexane, heptane, toluene, $iPr_2O$, MeOtBu or their mixtures; more particularly, cyclohexane, heptane; and even more particularly, heptane.

Therefore, the invention provides 3-carboxylic esters of allopregnanolone of high purity level, comprising an amount of 5α-pregn-2-en-20-one not higher than 0.5% (e.g. about 0.5% or below, 0.4% or below, 0.3% or below, 0.2% or below, 0.1% or below).

Hydrolysis of 3-Esters of Allopregnanolone to Allopregnanolone

The inventors have found that the hydrolysis of certain 3-esters of allopregnanolone (e.g. the esters of acetic, formic, isobutyric, benzoic, orto methoxy benzoic, or 3- or 4-nitrobenzoic acid) generates large amounts of 3α-hydroxy-5α,17α-pregnan-20-one (herein also referred to as impurity II or epimeric impurity):

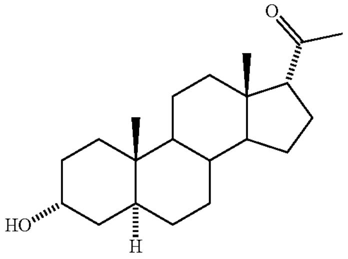

Epimeric impurity II $^1H$ NMR (400 MHz, $CDCl_3$): δ 4.00 (1H), 2.77 (1H), 2.10 (3H), 1.84-1.94 (1H), 1.53-1.79 (6H), 1.33-1.5 (6H), 1.07-1.33 (8H), 0.94-1.04 (1H), 0.89 (3H), 0.75 (3H), 0.67-0.63 (1H).

$^{13}C$ NMR (400 MHz, $CDCl_3$): δ 212.9, 66.5, 61.5, 53.6, 50.4, 45.9, 39.1, 36.2, 36.0, 35.8, 35.5, 32.9, 32.3, 32.2, 29.0, 28.6, 25.9, 24.4, 21.1, 20.8, 11.2.

In the interest of a purification suitable at commercial scale, it is convenient to keep the level of 3α-hydroxy-5α,17α-pregnan-20-one not higher than 0.5% during the hydrolysis reaction. This may be successfully achieved with 3-esters of allopregnanolone derived from carboxylic acids having a low pka (e.g. pka of 3 or less), which readily hydrolyze in the conditions disclosed in the present invention. Moreover, if obtained according to the process disclosed hereinabove, such 3-esters of allopregnanolone also contain low amounts of 5α-pregn-2-en-20-one 0.5%).

In the present invention, the hydrolysis is carried out under neutral conditions (e.g. in the presence of an alcohol without adding any acid or base), mild basic conditions (e.g. in the presence of a base whose conjugate acid has a pKa≤11) or energetic basic conditions (e.g. in the presence of a base whose conjugate acid has a pKa≥12 for unprolonged times and/or at not high temperatures).

According to a particular embodiment, the ester is hydrolyzed under neutral conditions employing an alcohol selected from methanol, ethanol, propanol, isopropanol, sec-butanol, and t-butanol. More particularly, the alcohol is MeOH or EtOH. In an embodiment, the ester is stirred in alcohol for sufficient time (e.g. about 1-24 h, or about 1-12 h) and at suitable temperature (e.g. about 15-40° C. or about 15-25° C.) for the completion of the hydrolysis. The reaction may be followed by thin layer chromatography (TLC).

According to a particular embodiment, the ester is hydrolyzed under mild basic conditions employing a base selected from alkali and alkaline earth carbonates and bicarbonates such as potassium carbonate, sodium carbonate, barium carbonate, cesium carbonate, potassium hydrogenocarbonate, and sodium hydrogenocarbonate. More particularly, the base is potassium carbonate, sodium carbonate, potassium hydrogenocarbonate, or sodium hydrogenocarbonate, and even more particularly, the base is potassium carbonate, sodium carbonate. This reaction may be carried out in the presence of an alcohol such as methanol, ethanol, propanol, isopropanol, sec-butanol, or t-butanol as solvent. In an embodiment, the alcohol is MeOH or EtOH. In an embodiment, the ester is treated with any of the mentioned bases, preferably in an amount of about 0.2-3 eq. or about 0.5-2 eq., at a suitable temperature of about 15-40° C. or about 15-30° C. for time sufficient for hydrolysis, normally between about 1-4 h. In an embodiment, the reaction mixture may be stirred for sufficient time (e.g. about 1-4 h) and at suitable temperature (e.g. about 15-40° C. or about 15-30° C.) for the completion of the hydrolysis.

According to a particular embodiment, the ester is hydrolyzed under energetic basic conditions employing a base selected from alkali and alkaline earth $C_{1-6}$ alkoxides and hydroxides. More particularly, the base is potassium methoxide, sodium methoxide, potassium ethoxide, sodium ethoxide, lithium hydroxide, potassium hydroxide, sodium hydroxide, and calcium hydroxide, and even more particularly, the base is sodium methoxide, potassium hydroxide, or sodium hydroxide. This reaction may be carried out in the presence of an alcohol such as methanol, ethanol, propanol, isopropanol, sec-butanol, or t-butanol as solvent. In an embodiment, the alcohol is MeOH or EtOH The use of strong bases (pKa equal or above 12) requires keeping the hydrolysis reaction for short times and/or at low temperatures so as to prevent that 3α-hydroxy-5α,17α-pregnan-20-one is generated in an amount higher than 0.5%. In an embodiment, the hydrolysis under energetic basic conditions is carried out for not more than about 2 h, more particularly not more than about 1.5 h and even more particularly not more than about 1 h and/or at a temperature of about 15-40° C., more particularly about 15-30° C. In an embodiment, the ester is treated with any of the mentioned bases, preferably in an amount of about 5-15 eq. or about 10 eq, at a suitable temperature of about 15-40° C. or about 15-30° C. for time sufficient for hydrolysis (e.g. not more than about 2 h, more particularly not more than about 1.5 h and even more particularly not more than about 1 h). In an embodiment, the reaction mixture may be stirred for sufficient time (e.g. about 0.5-2 h) and at suitable temperature (e.g. not higher than 40° C. or 30° C.) for the completion of the hydrolysis.

Advantageously, allopregnanolone is obtained in high purity, comprising an amount of 3α-hydroxy-5α,17α-pregnan-20-one (herein also referred to as impurity II or epimeric impurity) not higher than 0.5% (e.g. about 0.5% or below, 0.4% or below, 0.3% or below, 0.2% or below, 0.1% or below).

Isolation of allopregnanolone may be carried out for instance by precipitation in a solvent system comprising water and an organic solvent. Preferably, the organic solvent used for precipitating the crude allopregnanolone is a water-soluble solvent such as cyclic and acyclic ethers (e.g. 1,4-dioxane), ketones (e.g. acetone, methyl ethyl ketone), nitriles (e.g. acetonitrile, propionitrile), amides (e.g. DMF, DMA, HMPA), alcohols (e.g. methanol, ethanol, propanol, isopropanol, sec-butanol, t-butanol), and mixtures thereof. More particularly, the water-soluble solvent is selected from 1,4-dioxane, acetone, acetonitrile, DMF, methanol, ethanol, isopropanol or their mixtures, even more particularly the water-soluble solvent is 1,4-dioxane, acetonitrile or methanol, and even still more particularly, it is methanol.

Different proportions of water and organic solvent may be used. According to one embodiment, the ratio water to organic solvent within the solvent system ranges from about 0.1:1 to 1:0.1, more particularly about 0.2:1 to 1:0.2, 0.3:1 to 1:0.3, 0.4:1 to 1:0.4, 0.5:1 to 1:0.5, 0.6:1 to 1:0.6, 0.7:1 to 1:0.7, 0.8:1 to 1:0.8, 0.9:1 to 1:0.9, and about 1:1.

In more specific embodiment, crude allopregnanolone may be conveniently precipitated with a solvent system comprising water and an organic solvent at a ratio about 0.5:1, wherein the organic solvent is 1,4-dioxane, acetonitrile or methanol.

Once precipitated, allopregnanolone is preferably dried (e.g. under reduced pressure).

If desired, further purification of allopregnanolone may be effected for instance using recrystallization. Examples of solvents useful for inducing crystal formation include, but are not limited to hydrocarbon solvents (e.g. pentane, hexane, cyclohexane, heptane), aromatic solvents (e.g. toluene, xylene), ketones (e.g. acetone, methyl ethyl ketone), esters (e.g. EtOAc, iPrOAc), nitriles (e.g. acetonitrile, propionitrile), alcohols (e.g. methanol, ethanol, propanol, isopropanol), and mixtures thereof. In a particular embodiment, the non-polar solvent is selected from MeOH, EtOH, IPA, acetone, ACN etc, and even more particularly, MeOH/water.

Advantageously, the recrystallization allows eliminating or reducing the level of impurities so as to obtain allopregnanolone of high purity level, comprising an amount of 5α-pregn-2-en-20-one and 3α-hydroxy-5α,17α-pregnan-20-one, in total, of 0.15% or less. In preferred variants of the invention, the amount of said both impurities in the final allopregnanolone is at most 0.10%.

The present invention allows obtaining allopregnanolone with a high degree of purity such as above 98%, above 99% and even above 99.5%, complying with the requirements normally imposed by Good Manufacturing Practices (GMP) for Pharmaceutical Products. In a particular embodiment, the purity of allopregnanolone is ≥99.5% and the total content of impurities I and II is equal or below 0.15%, preferably equal or below 0.10%.

In a preferred embodiment of the present invention, allopregnanolone is prepared by a process comprising the following steps:

- reacting isoallopregnanolone with a strong carboxylic acid under Mitsunobu conditions;
- precipitating the 3-carboxylic ester of allopregnanolone in a solvent system comprising water and an organic solvent;
- recrystallizing the precipitate of the 3-carboxylic ester of allopregnanolone in a non-polar solvent;
- subjecting the 3-carboxylic ester of allopregnanolone thus obtained to hydrolysis under neutral conditions, mild basic conditions or energetic basic conditions to afford allopregnanolone; and
- precipitating and recrystallizing thereby obtaining allopregnanolone with a total content of impurities I and II, in total, of 0.15% or below.

The present disclosure provides allopregnanolone with a total content of impurities I and II equal or below 0.15% for use in the preparation of pharmaceutical compositions. The present disclosure also encompasses the use of allopregnanolone with a total content of impurities I and II equal or below 0.15% for the preparation of pharmaceutical compositions. The present disclosure comprises processes for preparing the above mentioned pharmaceutical compositions. The processes comprise combining allopregnanolone with a total content of impurities I and II equal or below 0.15% with at least one pharmaceutically acceptable excipient. Allopregnanolone and the pharmaceutical compositions of allopregnanolone of the present disclosure can be used as medicaments, particularly for the treatment of postpartum depression (PPD). The present disclosure also provides methods of treating of postpartum depression (PPD) comprising administering a therapeutically effective amount of allopregnanolone of the present disclosure to a subject in need of the treatment.

3-Esters of Allopregnanolone

In another aspect, the present invention provides the following 3-esters of allopregnanolone:

Pregnan-20-one, 3-(2,6-dinitrobenzoyloxy)-, (3α,5α)-
Pregnan-20-one, 3-(2,4-dinitrobenzoyloxy)-, (3α,5α)-
Pregnan-20-one, 3-(chloroacetyloxy)-, (3α,5α)-
Pregnan-20-one, 3-(dichloroacetyloxy)-, (3α,5α)-
Pregnan-20-one, 3-(trichloroacetyloxy)-, (3α,5α)-
Pregnan-20-one, 3-(cyanoacetyloxy)-, (3α,5α)-
Pregnan-20-one, 3-(fluoroacetyloxy)-, (3α,5α)-
Pregnan-20-one, 3-(difluoroacetyloxy)-, (3α,5α)-
Pregnan-20-one, 3-(2-nitrobenzoyloxy)-, (3α,5α)-

These esters may be prepared by reacting isoallopregnanolone with the corresponding carboxylic acid (i.e. 2,6-dinitrobenzoic, 2,4-dinitrobenzoic, chloroacetic, dichloroacetic, trichloroacetic, cyanoacetic, fluoroacetic, difluoroacetic, or 2-nitrobenzoic acid) under Mitsunobu conditions.

It should be understood that the scope of the present disclosure includes all the possible combinations of embodiments disclosed herein.

The following examples are merely illustrative of certain embodiments of the invention and cannot be considered as restricting it in any way.

EXAMPLES

1.—Conversion of Isoallopregnanolone into α-3-Chloroacetate Ester of Brexanolone

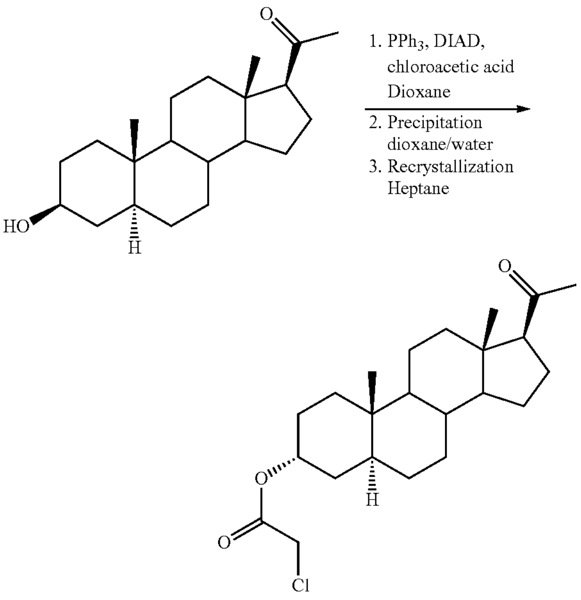

Mitsunobu: Isopregnanolone (36 g, 113.2 mmol), $PPh_3$ (43.2 g, 1.5 eq) and chloroacetic acid (27 g, 2.5 eq) were suspended in 1,4-dioxane (400 mL). The mixture was cooled at 15° C. and a solution of DIAD (32.4 mL, 1.4 eq) in dioxane (140 mL) was added dropwise. At the end of addition the reaction mass was stirred at 35° C. until the reaction was finished (4 h). Elimination Impurity I (5α-pregn-2-en-20-one): about 9-12%.

Work-up and isolation: After cooling down at 25° C., water (540 mL) was added and the resulting suspension was stirred 30 min and then cooled to 20-25° C. The suspension was filtered and the wet cake washed with 100 mL of a mixture dioxane/water 1:1. The product was dried at 50° C. under reduced pressure giving place to 32.45 g of a white solid (yield: 70%; purity: 96%). Elimination Impurity I (5α-pregn-2-en-20-one): 3.5%.

Recrystallization: The obtained dry cake was suspended in heptane (15 ml/g) and heated at 75° C. till complete dissolution. The solution was then cooled at 0/10° C. and the precipitated was filtered off. The solid was washed with fresh heptane (2 ml/g), and dried at 50° C. under reduced pressure. Weight: 29.2 g; Yield: 90%; Purity: 99.15%. Elimination Impurity I (5α-pregn-2-en-20-one): 0.3%.

$^1$H NMR (400 MHz, $CDCl_3$): δ 5.07 (1H), 4.02 (2H), 2.40 (1H), 2.09-2.15 (1H), 2.07 (3H), 1.95-1.99 (1H), 1.72-1.95 (1H), 1.54-1.68 (4H), 1.44-1.51 (4H), 1.28-1.42 (3H), 1.08-1.26 (6H), 0.85-0.96 (1H), 0.72-0.81 (4H), 0.56 (3H).

$^{13}$C NMR (400 MHz, $CDCl_3$): δ 209.5, 166.7, 72.6, 63.8, 56.7, 54.0, 44.2, 41.4, 39.9, 39.0, 35.8, 35.4, 32.8, 32.7, 31.8, 31.5, 28.2, 26.0, 24.4, 22.8, 20.8, 13.5, 11.4.

Isolation of 5α-pregn-2-en-20-one from the dioxane/water mother liqueurs obtained in the ester precipitation: The mother liqueurs were diluted with more water (around 3 Liters), a suspension was formed and the solid was isolated by filtration. The filtrate was suspended in 400 ml of Heptane, stirred during one hour at 40° C. and filtered again, the liquid was evaporated to get also a solid that was submitted to chromatography and characterized by NMR:

$^1$H NMR (400 MHz, $CDCl_3$): δ 5.57 (2H), 2.50 (1H), 2.10-2.18 (1H), 2.09 (3H), 1.81-2.0 (3H), 1.51-1.71 (5H), 1.07-1.43 (9H), 0.83-0.94 (1H), 0.75-0.76 (1H), 0.73 (3H), 0.59 (3H).

$^{13}$C NMR (400 MHz, $CDCl_3$): δ 209.7, 125.9, 125.8, 63.9, 56.8, 54.0, 44.2, 41.5, 39.9, 39.2, 35.7, 34.7, 31.8, 31.6, 30.3, 28.7, 24.5, 22.9, 21.0, 13.5, 11.8.

NMR signal match with the data found in literature (Tetrahedron (60) 2004, 11851-11860).

2.—Hydrolysis of α-3-Chloroacetate Ester to Brexanolone

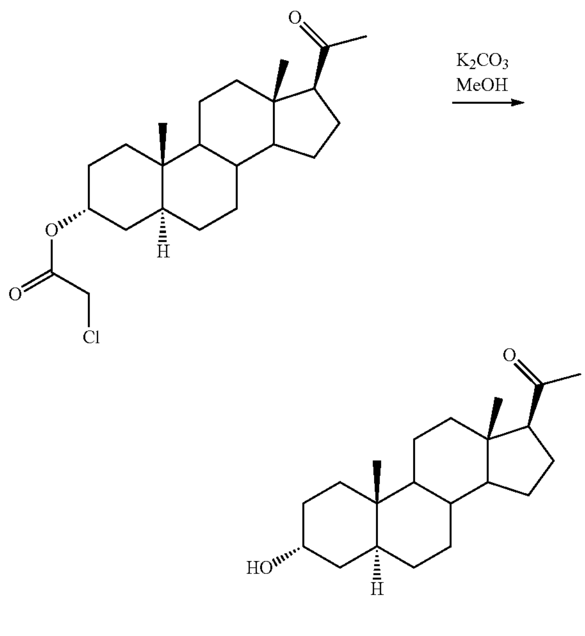

Hydrolysis: Chloroacetate-Brexanolone (29.2 g, 74.11 mmol) was suspended in methanol (300 mL) and potassium carbonate (5 g, 0.5 eq) was added. The reaction mixture was stirred for 1 h at 30° C.

Work-up and isolation: 150 ml of water were added and cooled down at 0/5° C. and the solid filtered. The wet cake was then washed with 60 mL of a mixture methanol/water 1:0.5. The product was dried at 50° C. under reduced pressure, affording 22 g of crude Brexanolone (yield: 93%; purity: >99%). Epimeric Impurity II (3α-hydroxy-5α,17α-pregnan-20-one): 0.23%.

Recrystallization: The obtained dry cake was suspended in MeOH (15 vol) and stirred during 30 min at 30° C., then water (7.5 vol) was added and the resulting suspension was cooled to 5-10° C. and filtered, the wet cake was dried, giving place to 20 g of pure brexanolone as a white solid (purity: >99.8%; DSC 176° C.), Epimeric Impurity II (3α-hydroxy-5α,17α-pregnan-20-one): 0.08%. Elimination Impurity I (5α-pregn-2-en-20-one) not detected.

3.—Hydrolysis of α-3-Chloroacetate Ester Containing 0.73% of the 5-α-Pregna-3-En-20-One (Comparative)

Hydrolysis: chloroacetate-brexanolone (5 g, 12.7 mmol with a 0.73% of elimination impurity by HPLC) was suspended in methanol (50 mL) and potassium carbonate (0.85 g, 0.5 eq) was added. The reaction mixture was stirred for 1 h at 20-25° C. (starting material content: 0.35%).

Work-up: 150 ml of water were added and cooled down at 0/5° C. and the solid filtered. The wet cake was then washed with 7.5 mL of a mixture methanol/water 1:0.5. The product was dried at 50° C. under reduced pressure to obtain 3.77 g of crude brexanolone (yield: 93%; purity: >98.93%). Elimination impurity I (5α-pregn-2-en-20-one): 0.52%.

Recrystallization: The obtained dry cake was suspended in MeOH (25 vol) and dissolved at 35-40° C. The reaction mixture was cooled to 20-25° C., and then water (12.5 vol) was slowly added giving place to a suspension which was filtered. The wet cake was dried, resulting in 3.3 g of brexanolone as a white solid. Purity>99.7%, Elimination impurity I (5-α-pregna-3-en-20-one): 0.21%.

Thus starting from an ester containing more than 0.5% of elimination impurity I it was not possible to lower the amount of the same below 0.15%.

4.—Hydrolisis of α-3-Chloroacetate Ester Containing 0.5% of Impurity 5α-Pregn-2-En-20-One The process disclosed in example 3 was followed but using α-3-chloroacetate ester containing 0.5% of elimination impurity I as starting material. It was obtained 3.2 g brexanolone with a purity of >98% and a content of elimination impurity I of about 0.13%.

Thus starting from an ester containing 0.5% of elimination impurity I it was possible to lower the amount of the same below 0.15%.

5.—Hydrolysis of α-3-Chloroacetate Ester Containing 0.5% of 3α-Hydroxy-5α,17α-Pregnan-20-One Hydrolysis: Chloroacetate-Brexanolone (5 g, 12.7 mmol doped with 0.5% of the epimeric impurity) was suspended in methanol (50 mL) and potassium carbonate (0.85 g, 0.5 eq) was added. The reaction mixture was stirred for 1 h at 20-25° C. (starting material content: 0.30%), Work-up: 150 ml of water were added and cooled down at 0/5° C. and the solid filtered. The wet cake was then washed with 7.5 mL of a mixture methanol/water 1:0.5. The product was dried at 50° C. under reduced pressure to obtain 3.82 g of crude brexanolone (yield: 94%; purity: >99.43%). Epimeric impurity II (3α-hydroxy-5α,17α-pregnan-20-one): 0.24%. Elimination impurity I (5α-pregn-2-en-20-one): 0.18%.

Recrystallization: The obtained dry cake was suspended in MeOH (25 vol) and dissolved at 35-40° C., the reaction mixture was cooled to 20-25° C., then water (12.5 vol) was slowly added giving place to a suspension which was filtered, the wet cake was dried, resulting in 3.3 g of Brexanolone as a white solid. Purity: 99.81%. Epimeric impurity II (3α-hydroxy-5α,17α-pregnan-20-one): 0.1%. Elimination impurity I (5α-pregn-2-en-20-one): 0.02%.

6.—Conversion of Isoallopregnanolone into α-3-Chloroacetate Ester of Brexanolone

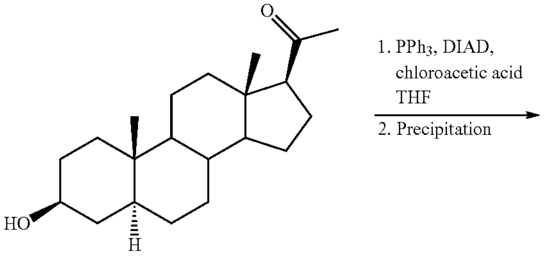

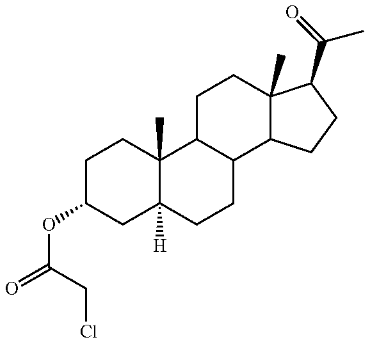

Mitsunobu: Isopregnanolone (14 g, 44 mmol), $PPh_3$ (16.8 g, 1.5 eq) and chloroacetic acid (10.5 g, 2.5 eq) were suspended in THF (140 mL). The mixture was cooled at 15° C. and a solution of DIAD (32.4 mL, 1.4 eq) in dioxane (70 mL) was added dropwise. At the end of addition the reaction mass was stirred at 35° C. until the reaction has finished (4 h). Elimination Impurity I (5α-pregn-2-en-20-one): about 8%.

After cooling down at 25° C., the reaction mass (250 ml), was divided into 7 samples (35 ml each, containing about 2 g of the ester final product). Every sample was subjected to evaporation, the residue was redissolved again in 30 ml of different kind of solvents miscible with water (MeOH, ACN, DMF, IPA, Acetone, Dioxane) and induced precipitation with the same volume of water.

7.—Conversion of Isoallopregnanolone into α-3-Trifluororoacetate Ester of Brexanolone

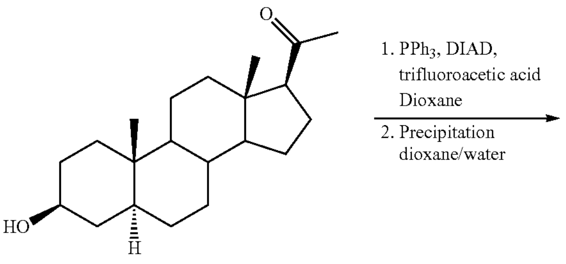

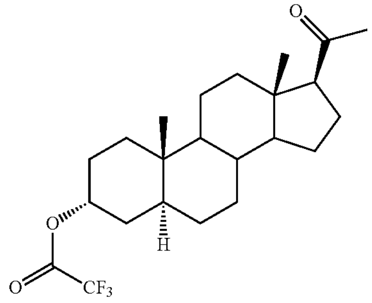

Mitsunobu: Isopregnanolone (1 g, 3.14 mmol), $PPh_3$ (1.2 g, 1.5 eq) and trifluoroacetic acid (0.6 ml, d=1.489, 2.5 eq) were suspended in 1,4-dioxane (10 mL). The mixture was cooled at 15° C. and a solution of DIAD (0.9 mL, 1.4 eq) in dioxane (5 mL) was added dropwise. At the end of addition the reaction mass was stirred at 35° C. during one hour and then 1.2 eq of NaOBz were added as a solid and the reaction mixture was stirred again at 35° C. during 20 h (starting material still 6%).

Work-up and precipitation: After cooling down at 25° C., water (10 mL) was added and the resulting suspension was stirred 30 min then cooled to 10-15° C. The suspension was filtered and the wet cake washed with 2 mL of a mixture dioxane/water 1:1. The product was dried at 50° C. under reduced pressure giving place to 0.75 of the ester, elimination impurity amount 14.6% by HPLC.

8.—α-3-Benzoyl Ester of Brexanolone (Comparative)

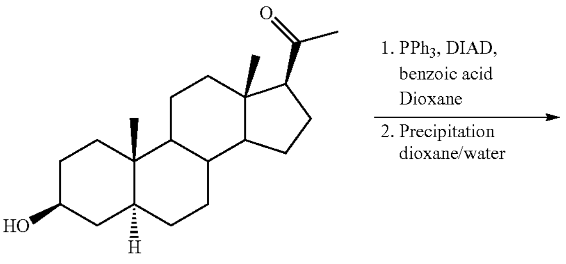

-continued

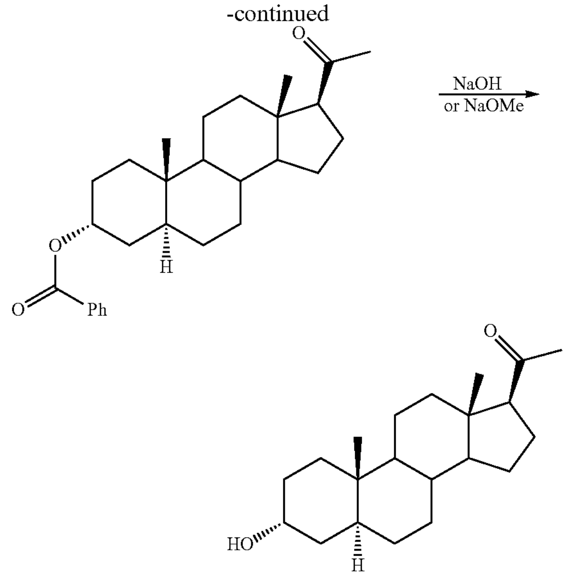

Mitsunobu: Isopregnanolone (1 g, 3.14 mmol), $PPh_3$ (1.2 g, 1.5 eq) and benzoic acid (0.6 g, 2.5 eq) were suspended in 1,4-dioxane (10 mL). The mixture was cooled at 15° C. and a solution of DIAD (0.9 mL, 1.4 eq) in dioxane (5 mL) was added dropwise. At the end of addition the reaction mass was stirred at 35° C. during 5 hours (elimination impurity amount about 8%).

Work-up and precipitation After cooling down at 25° C., water (10 mL) was added and the resulting suspension was stirred 30 min then cooled to 10-15° C. The suspension was filtered and the wet cake washed with dioxane/water 1:1. The product was dried at 50° C. under reduced pressure giving place to 0.1 g of the ester of >96% (elimination impurity 0.5%).

Hydrolisis.—The benzoyl ester was added to a solution of 70 vol of MeOH and 12 eq of NaOH, the reaction mixture was warmed at 40° C. for 30 h, a sample was taken and analyzed by HPLC, there was only 4% of the brexanolone final product and 9% of the Epimeric impurity together with the ester starting material.

As may also be appreciated in this example and also from example 12, the benzoyl ester of brexanolone cannot afford brexanolone with an acceptable level of purity.

9.—Brexanolone from Isopregnanolone in a "One-Pot" Process Using Chloroacetic Acid (Comparative)

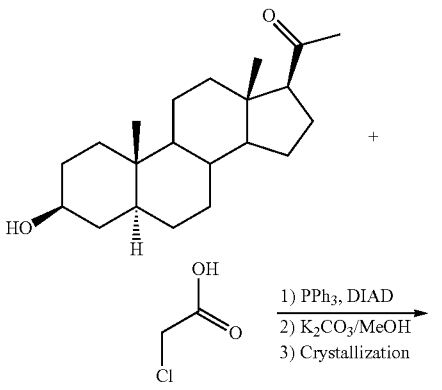

-continued

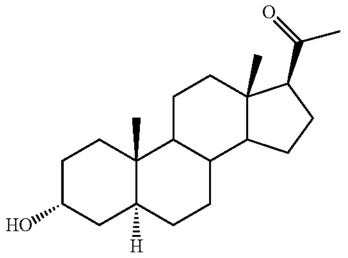

Triphenyl phosphine (1.2 g/g), chloroacetic acid (0.75 g/g) and isopregnanolone were loaded in a round bottom flask, followed by toluene (10 ml/g). The suspension was cooled at 15° C. and a solution of DIAD (0.95 ml/g) in toluene (5 ml/g) was added dropwise, keeping the temperature below 25° C. The resulting yellow solution was heated at 35° C. during 4 h. After consumption of starting material (K1), a solution of $NaHCO_3$ 7% aq (5 ml/g) was added. The organic phase was later washed with water (5 ml/g) and evaporated to reduced pressure. The traces of toluene were removed by further distillation with methanol. The ester residue was suspended in methanol (10 ml/g) and potassium carbonate (0.17 g/g) was added. The suspension stirred at 30° C. during 1 h (K2). The product was then precipitated by addition of water (5 ml/g). The reaction mass was cooled at 5° C., filtered and washed with a mixture methanol/water 1:0.5 (2 ml/g) (TH1). The resulting wet cake was further washed with heptane (5 ml/g) (TH2).

| Sample | 5α-Pregn-2-en-20-one (HPLC %) | UV factor |
|---|---|---|
| K1 | 16 | 0.5 |
| K2 | 14 | 0.7 |
| TH1 | 14 | 0.7 |
| TH2 | 9 | 0.7 |

As may be appreciated, the one-pot process leads to an elevated amount of elimination impurity (9%) which cannot be separated from brexanolone.

10.—Brexanolone from Isopregnanolone in a "One-Pot" Process Using Trifluoroacetic Acid and Purifying by Chromatography (Comparative)

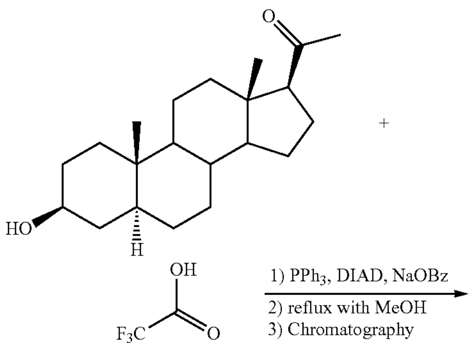

-continued

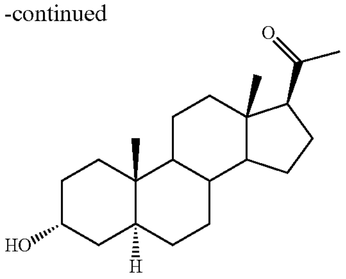

Triphenyl phosphine (1.2 g), trifluoro acetic acid (0.6 ml, 2.5 eq), NaOBz (0.9 g) and isopregnanolone (1 g) were loaded in a round bottom flask, followed by THF (10 ml). The suspension was cooled at 15° C. and a solution of DIAD (0.95 ml) in THF (5 ml) was added dropwise, keeping the temperature below 25° C. The resulting reaction mass was kept stirring at 25° C. during 24 h. After consumption of starting material the reaction mixture was evaporated to residue under reduced pressure.

MeOH (20 ml) was added and the mixture was refluxed for 24 h, the solvent was evaporated and the residue was purified by column chromatography column to obtain 0.69 g of Brexanolone, purity: 97%.

As may be appreciated, the one-pot process leads to brexanolone with a low level of purity.

11.—Brexanolone Acetate Using Toluene as Solvent and Sodium Benzoate (Comparative)

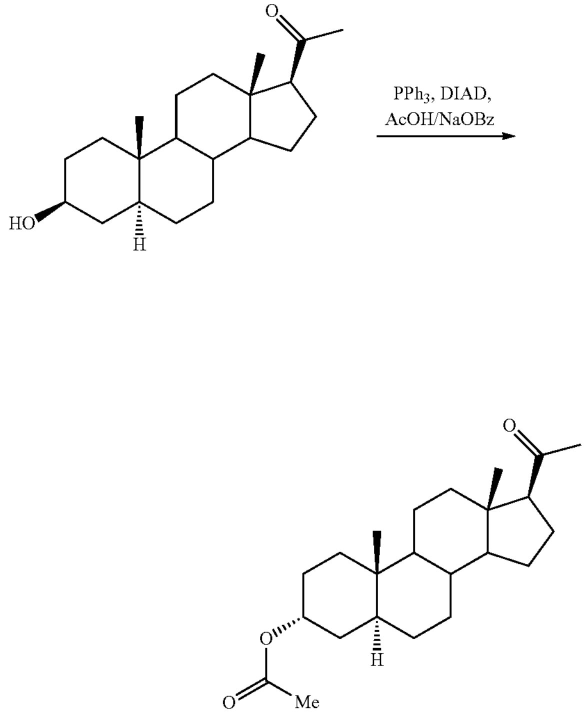

DIAD (0.46 g), acetic acid (0.15 ml), and isopregnanolone (0.5 g) and toluene (15 ml) were loaded in a round bottom flask. The reaction mass was cooled at 0° C. and $PPh_3$ (0.6 g) followed by NaOBz (0.34 g) was added. The resulting reaction mass was kept stirring at 25° C. during 15 h. After consumption of starting material the reaction mixture was evaporated to residue under reduced pressure (elimination impurity content around 14%).

This example shows that elimination impurity is intrinsic to the Mitsunobu reaction.

12.—Benzoate, Nitrobenzoate, 2,6-Dinitrobenzoate Ester Hydrolysis

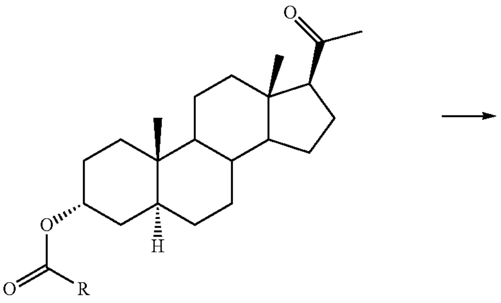

394
Brexanolone-ester

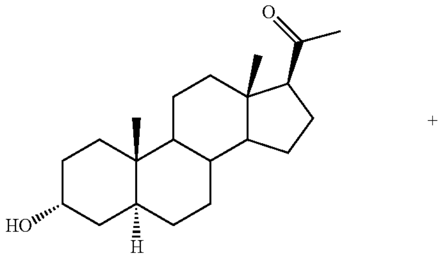

318
Brexanolone

+

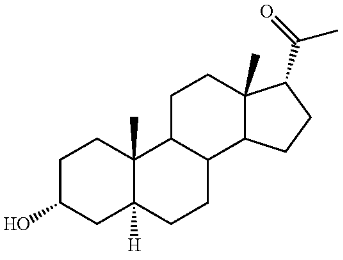

Epimer

| Ester | Base/solvent | Time/T[a] | Ester/FP/ epimer | Comments |
|---|---|---|---|---|
| 1)Benzoate. pKa benzoic acid: 4.2 | NaOH (12 eq)/MeOH (70 vol) | 30 h/40° C. | 87%/4%/9% | No significant hydrolysis even with strong base but a lot of epimer was already achieved. |
| 2)Benzoate pKa benzoic acid: 4.2 | KOH (12 eq)/ MeOH (70 vol) | 30 h/40° C. | 87%/4%/9% | Same comments with KOH |
| 3) Benzoate pKa benzoic acid: 4.2 | MeONa (10 eq)/MeOH (50 vol) | 6 h/30° C. | 17%/71%/14% | Hydrolysis partially performed but with significant amount of epimer. |
| 4) Benzoate pKa benzoic acid: 4.2 | SO4H2 (10 eq)/MeOH (25 vol) | 0.5 h/RT | 0%/92%/8% | Hydrolysis completed but with significant amount of epimer. |
| 5) 4-nitro-benzoate pKa 4-NO2-benzoic acid: 3.4 | NaOH(10 eq)/ MeOH (40 vol) | 4.5 h/30° C. | 67%/31%/2% | Hydrolysis only partially performed |
| 6) 4-nitro-benzoate pKa 4-NO2-benzoic acid: 3.4 | NaOH(10 eq)/ MeOH (40 vol) | 15 h/30° C. | 0%/85%/14% | Hydrolysis completed but with significant amount of epimer. |
| 7) 2,6-dinitrobenzoate pKa dinitrobenzoic acid: 1.14 | NaOH(10 eq)/ MeOH (40 vol) | 1 h/30° C. | 0%/100%/0% | Hydrolysis completed no epimer was detected. |

As can be seen in the table, neither the benzoic ester nor the 4-nitrobenzoic ester hydrolyze easily, requiring very energetic conditions that cause the formation of the epimer (difficult to purify). The dinitrobenzoic ester, however, hydrolyzes in only one hour without giving the epimer.

13.—Hydrolysis of Alpha-3-Acetate Ester to Achieve Brexanolone. (Comparative)

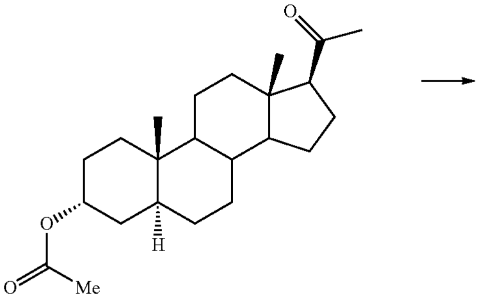

394
Brexanolone-acetate

-continued

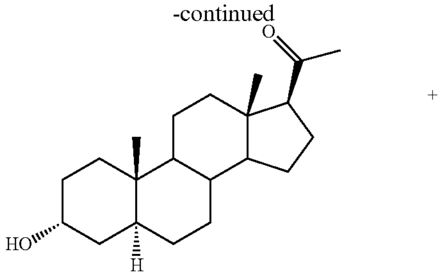

318
Brexanolone

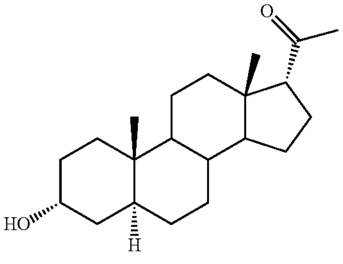

Epimer

In a round bottom flask, 3-alpha acetate-pregnanolone (1 g), was dissolved in 15 mL of methanol. 0.26 g of sodium hydroxide (2.4 eq) were added, and the reaction mass was stirred at 40° C. for 4 h. HPLC control showed disappearance of starting material. The solvent was concentrated under reduced pressure till a volume of 5 mL. The mixture was poured into water (87 mL), and stirred at room temperature for 1 hour.

The precipitate was then filtered and the wet cake was washed with water (10 mL) and dried under vacuum at 50° C.

An analysis by HPLC of the solid revealed the presence of 8.6% of the epimeric impurity (II).

14.—3-(2,4-Dinitrobenzoyl Ester) of Brexanolone

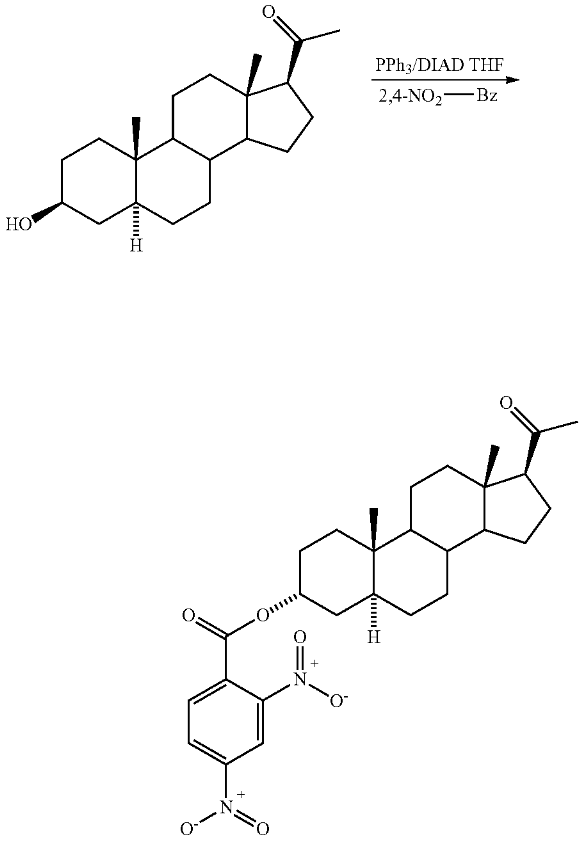

Isopregnanolone (0.5 g, 1.57 mmol), $PPh_3$ (0.6 g, 1.5 eq) and 2,4-nitrobenzoic acid (0.5 g, 2.5 eq) were suspended in THF (10 mL). The mixture was cooled at 0/5° C. and a solution of DIAD (0.45 mL, 1.4 eq) in THF (5 mL) was added dropwise. At the end of addition, the reaction mass was stirred at room temperature during 5 hours. Water 1 mL was added, the solvent was evaporated and the residue was purified by column chromatography. 0.24 g of solid product were obtained (yield 32.7%).

15.—3-(3,5-Dinitrobenzoyl Ester) of Brexanolone

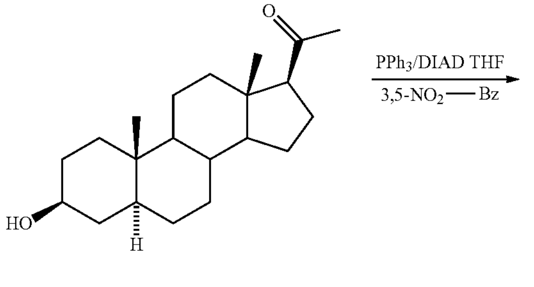

-continued

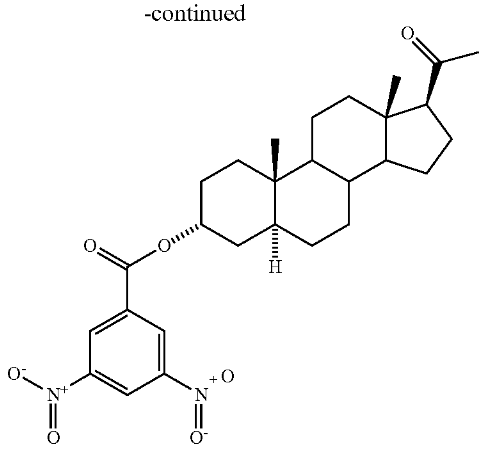

Isopregnanolone (0.5 g, 1.57 mmol), $PPh_3$ (0.6 g, 1.5 eq) and 3,5-dinitrobenzoic acid (0.5 g, 2.5 eq) were suspended in THF (10 mL). The mixture was cooled at 0/5° C. and a solution of DIAD (0.45 mL, 1.4 eq) in THF (5 mL) was added dropwise. At the end of addition, the reaction mass was stirred at room temperature during 5 hours. Water 1 mL was added, the solvent was evaporated and the residue was purified by column chromatography. 0.43 g of solid product were obtained (yield 53.5%).

With the same procedure, 2-nitrobenzoyl ester of Brexanolone and 2,6-dinitrobenzoyl ester of Brexanolone were prepared.

16.—3-Dichloroacetic Ester of Brexanolone

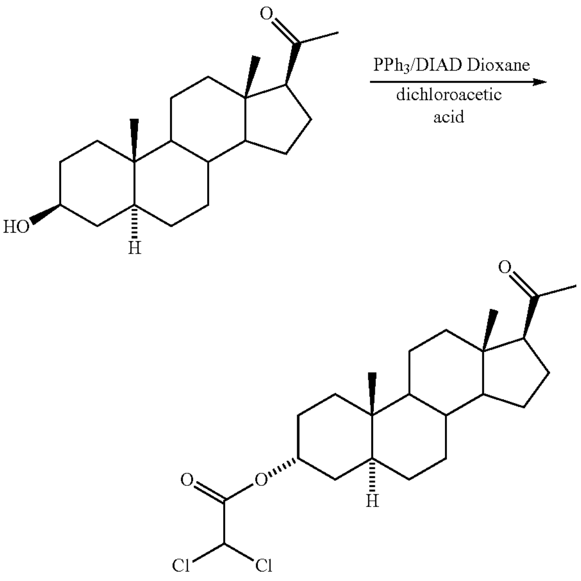

Isopregnanolone (5.0 g, 15.7 mmol), $PPh_3$ (6.0 g, 1.5 eq) and dichloroacetic acid (3.4 mL) were suspended in Dioxane (55 mL). The mixture was cooled at 15° C. and a solution of DIAD (4.5 mL, 1.4 eq) in Dioxane (20 mL) was added dropwise. At the end of addition, the reaction mass was stirred at 35° C. until completion. Water 75 mL were added, the mixture was stirred for 0.5 h, filtered off and washed with 10 mL (1:1) water/Dioxane and dried. 3.8 g of white solid product were obtained (yield 56.4%).

17.—3-Trichloroacetic Ester of Brexanolone

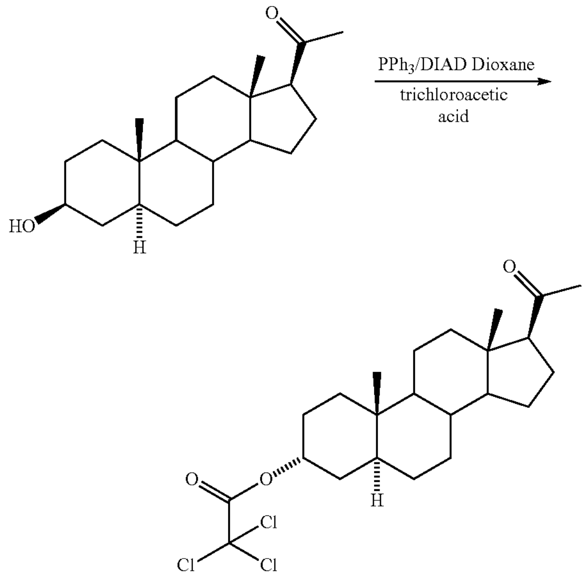

Isopregnanolone (5.0 g, 15.7 mmol), $PPh_3$ (6.0 g, 1.5 eq) and trichloroacetic acid (6.45 g) were suspended in Dioxane (55 mL). The mixture was cooled at 15° C. and a solution of DIAD (4.5 mL, 1.4 eq) in Dioxane (20 mL) was added dropwise. At the end of addition, the reaction mass was stirred at 35° C. until completion. Water 75 mL were added, the two phases were separated and the aqueous layer was extracted with 50 mL DCM. The organic layer was concentrated to obtain a yellow oil.

The invention claimed is:

1. A 3-carboxylic ester of allopregnanolone selected from:
Pregnan-20-one, 3-(2,6-dinitrobenzoyloxy)-, (3α,5α)-,
Pregnan-20-one, 3-(2,4-dinitrobenzoyloxy)-, (3α,5α)-,
Pregnan-20-one, 3-(chloroacetyloxy)-, (3α,5α)-,
Pregnan-20-one, 3-(dichloroacetyloxy)-, (3α,5α)-,
Pregnan-20-one, 3-(trichloroacetyloxy)-, (3α,5α)-,
Pregnan-20-one, 3-(fluoroacetyloxy)-, (3α,5α)-,
Pregnan-20-one, 3-(difluoroacetyloxy)-, (3α,5α)-,
Pregnan-20-one, 3-(2-nitrobenzoyloxy)-, (3α,5α)-, or
Pregnan-20-one, 3-(cyanoacetyloxy)-, (3α,5α)-.

2. A 3-carboxylic ester of allopregnanolone comprising the carboxylate of a carboxylic acid having a pKa of 3 or less, said ester containing an amount of 5α-pregn-2-en-20-one of 0.5% or less, wherein the carboxylic acid having a pKa≤3 is selected from the group consisting of monofluoroacetic acid, difluoroacetic acid, trifluoroacetic acid, monochloroacetic acid, dichloroacetic acid, trichloroacetic acid, cyanoacetic acid, 2-nitrobenzoic acid, 2,4-dinitrobenzoic acid, 2,6-dinitrobenzoic acid, and 3,5-dinitrobenzoic acid.

3. A process for preparing and purifying the 3-carboxylic ester of allopregnanolone of claim 2 which comprises:
reacting isoallopregnanolone with the carboxylic acid having a pKa≤3 under Mitsunobu conditions;
precipitating the 3-carboxylic ester of allopregnanolone in a solvent system comprising water and an organic solvent; and
recrystallizing the precipitate of the 3-carboxylic ester of allopregnanolone in a non-polar solvent.

4. The process according to claim 3, which further comprises preparing allopregnanolone by
subjecting the 3-carboxylic ester of allopregnanolone thus obtained to hydrolysis under neutral conditions, mild basic conditions or energetic basic conditions.

5. The process according to claim 3, wherein the 3-carboxylic ester of allopregnanolone is precipitated in a solvent system comprising water and a water-soluble organic solvent.

6. The process according to claim 3, wherein the 3-carboxylic ester of allopregnanolone is precipitated in a solvent system comprising water and a water-soluble organic solvent selected from 1,4-dioxane, acetone, acetonitrile, DMF, methanol, ethanol, isopropanol or their mixtures,
and/or
the precipitate of the 3-carboxylic ester of allopregnanolone is recrystallized in a non-polar solvent selected from group consisting of hexane, cyclohexane, heptane, toluene, $iPr_2O$, MeOtBu and mixtures thereof.

7. The process according to claim 4, wherein the 3-carboxylic ester of allopregnanolone is subjected to hydrolysis with an alcohol without adding any acid or base.

8. The process according to claim 4, wherein the 3-carboxylic ester of allopregnanolone is subjected to hydrolysis with a base whose conjugate acid has a pKa≤11.

9. The process according to claim 8, wherein the base whose conjugate acid has a pKa≤11 is an alkali or alkaline earth carbonate or bicarbonate.

10. The process according to claim 4, wherein the 3-carboxylic ester of allopregnanolone is subjected to hydrolysis with a base whose conjugate acid has a pKa≥12 for a time and at a temperature suitable to keep the level of 3α-hydroxy-5α, 17α-pregnan-20-one in an amount of 0.5% or less.

11. The process according to claim 10, wherein the base whose conjugate acid has a pKa≥12 is an alkali or alkaline earth $C_{1-6}$ alkoxide or hydroxide.

12. The process according to claim 10, wherein the hydrolysis is carried out for not more than about 2 h and/or at a temperature of about 15-40° C.

13. The process according to claim 4 which further comprises precipitating and recrystallizing the allopregnanolone thereby obtaining allopregnanolone with a total content of 5α-pregn-2-en-20-one and 3α-hydroxy-5α, 17α-pregnan-20-one, in total, of 0.15% or below.

* * * * *